(12) United States Patent
Bouzid

(10) Patent No.: US 9,541,750 B2
(45) Date of Patent: Jan. 10, 2017

(54) TELECENTRIC, WIDE-FIELD FLUORESCENCE SCANNING SYSTEMS AND METHODS

(71) Applicant: Ahmed Bouzid, Lincoln, NE (US)

(72) Inventor: Ahmed Bouzid, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 0 days.

(21) Appl. No.: 14/312,409

(22) Filed: Jun. 23, 2014

(65) Prior Publication Data
US 2015/0370058 A1    Dec. 24, 2015

(51) Int. Cl.
*G02B 17/00* (2006.01)
*G02B 21/16* (2006.01)
(Continued)

(52) U.S. Cl.
CPC ........... *G02B 21/16* (2013.01); *G01N 21/6456* (2013.01); *G02B 13/22* (2013.01);
(Continued)

(58) Field of Classification Search
CPC ....... G02B 13/00; G02B 21/361; G02B 17/08; G02B 21/24; G02B 21/22; G02B 21/06; G02B 21/10; G02B 21/082; G02B 23/14; G03F 7/70225; G03F 7/70233; G01J 3/02; G01J 3/46; G01N 21/67; G01N 21/6428; G01N 21/718
(Continued)

(56) References Cited

U.S. PATENT DOCUMENTS

| 3,641,344 A | 2/1972 | Markle |
| 5,198,577 A | 3/1993 | Denis et al. |

(Continued)

FOREIGN PATENT DOCUMENTS

| EP | 1256795 A2 | 11/2002 |
| EP | 1357553 A2 | 10/2003 |

(Continued)

OTHER PUBLICATIONS

Michel Doucet et al, Microscope with 3D mapping capabilities for planetary exploration applications, Proceedings of SPIE, vol. 8550, Dec. 18, 2012, pp. 855019-1-855019-1.
(Continued)

*Primary Examiner* — Stephone B Allen
*Assistant Examiner* — Rahman Abdur
(74) *Attorney, Agent, or Firm* — Leydig, Voit & Mayer, LTD; Gerald T. Gray

(57) ABSTRACT

Wide-field fluorescence imaging systems and methods. A bi-telecentric optical imaging system comprising imaging optics arranged and positioned such that a first telecentric space is created or exists between a sample platform and an entry aperture stop wherein Principal or chief rays from a plurality of field points on the sample platform are parallel to each other when passing through a first filter; and such that a second telecentric space is created or exists between a light detector and an exit aperture stop wherein the Principal or chief rays from the plurality of field points are parallel to each other when passing through a second filter. In this manner, light collected from different points in the field of view pass through the first filter at the same angles and also through the second filter at the same angles to thereby reduce or eliminate angular spectral shifting effects.

16 Claims, 7 Drawing Sheets

(51) Int. Cl.

| | |
|---|---|
| *G02B 21/04* | (2006.01) |
| *G02B 17/06* | (2006.01) |
| *G02B 13/22* | (2006.01) |
| *G02B 21/36* | (2006.01) |
| *G02B 21/00* | (2006.01) |
| *G01N 21/64* | (2006.01) |
| *G06F 15/173* | (2006.01) |
| *G06F 17/30* | (2006.01) |

(52) U.S. Cl.
CPC ....... *G02B 17/008* (2013.01); *G02B 17/0605* (2013.01); *G02B 17/0615* (2013.01); *G02B 21/002* (2013.01); *G02B 21/04* (2013.01); *G02B 21/361* (2013.01); *G06F 15/17306* (2013.01); *G06F 17/30595* (2013.01); *G06F 17/30867* (2013.01); *G01N 2021/6463* (2013.01); *G01N 2021/6478* (2013.01)

(58) Field of Classification Search
USPC ................. 359/362–366, 368, 369, 385, 387–390,359/432; 356/300, 311, 317, 318, 326, 328, 356/330, 331, 402, 405, 406, 407, 416, 419, 356/420; 250/226, 458.1, 459.1, 461.1
See application file for complete search history.

(56) References Cited

U.S. PATENT DOCUMENTS

| | | | |
|---|---|---|---|
| 5,206,699 | A | 4/1993 | Stewart et al. |
| 5,697,699 | A | 12/1997 | Seo et al. |
| 5,704,700 | A * | 1/1998 | Kappel .............. G02B 27/0927 345/31 |
| 6,252,664 | B1 | 6/2001 | Barbara-Gulliem |
| 6,345,115 | B1 | 2/2002 | Ramm et al. |
| 6,606,173 | B2 | 8/2003 | Kappel et al. |
| 6,621,615 | B2 | 9/2003 | Kruschwitz et al. |
| 6,917,696 | B2 | 7/2005 | Soenksen |
| 7,285,787 | B2 | 10/2007 | Horigome et al. |
| 7,457,446 | B2 | 11/2008 | Soenksen |
| 7,518,652 | B2 | 4/2009 | Olson et al. |
| 7,567,386 | B2 | 7/2009 | Lin |
| 7,993,927 | B2 | 8/2011 | Frangioni |
| 2001/0028458 | A1 | 10/2001 | Xiao |
| 2001/0030290 | A1 | 10/2001 | Stern |
| 2003/0007254 | A1 | 1/2003 | Tocci |
| 2005/0062963 | A1 | 3/2005 | Yoshida et al. |
| 2005/0151972 | A1 | 7/2005 | Boege et al. |
| 2005/0286047 | A1 * | 12/2005 | Boege ........................ G01J 3/02 356/317 |
| 2007/0154938 | A1 | 7/2007 | Oshida et al. |
| 2009/0080194 | A1 | 3/2009 | Bouzid et al. |
| 2011/0089315 | A1 * | 4/2011 | Walt .................. G02B 17/0615 250/251 |
| 2011/0121198 | A1 * | 5/2011 | Nakata ................. G02B 21/004 250/458.1 |
| 2011/0121199 | A1 * | 5/2011 | Tanikawa .................. G01J 3/02 250/458.1 |
| 2012/0313008 | A1 | 12/2012 | Jo et al. |
| 2013/0155499 | A1 * | 6/2013 | Dixon .................. G02B 21/002 359/385 |

FOREIGN PATENT DOCUMENTS

| | | |
|---|---|---|
| EP | 1681556 A1 | 7/2006 |
| EP | 2075615 A1 | 7/2009 |
| JP | 02-300616 A | 12/1990 |
| JP | 2000-162043 A | 6/2000 |
| JP | 2003-028799 A | 1/2003 |
| JP | 2004-286515 A | 10/2004 |
| JP | 2006-528772 A | 12/2006 |
| WO | WO 2004/017374 A2 | 2/2004 |

OTHER PUBLICATIONS

European Patent Office Search report, European Application No. 15173327.6, Nov. 16, 2015.
Hwang et al., "The Influence of Improved Interference Filter Performance for Molecular Imaging Using Frequency Domain Photon Migration Measurements", Optical Tomography and Spectroscopy of Tissue VI, SPIE vol. 5693, pp. 503-512, Apr. 2005.
Lichtman et al., "Fluorescence Microscopy," Nature Methods 2, pp. 910-919, Nov. 18, 2005.
Xenogen Product Sheet: IVIS® Imaging System 200 Series, 2004, 4 pages.
Japanese Patent Application No. 2008-555208, Notice of Rejection, dated Oct. 27, 2011, 4 pages.
International Search Report mailed on Feb. 22, 2007, for PCT Application No. PCT/US06/05341 filed on Feb. 15, 2008, 1 page.

\* cited by examiner

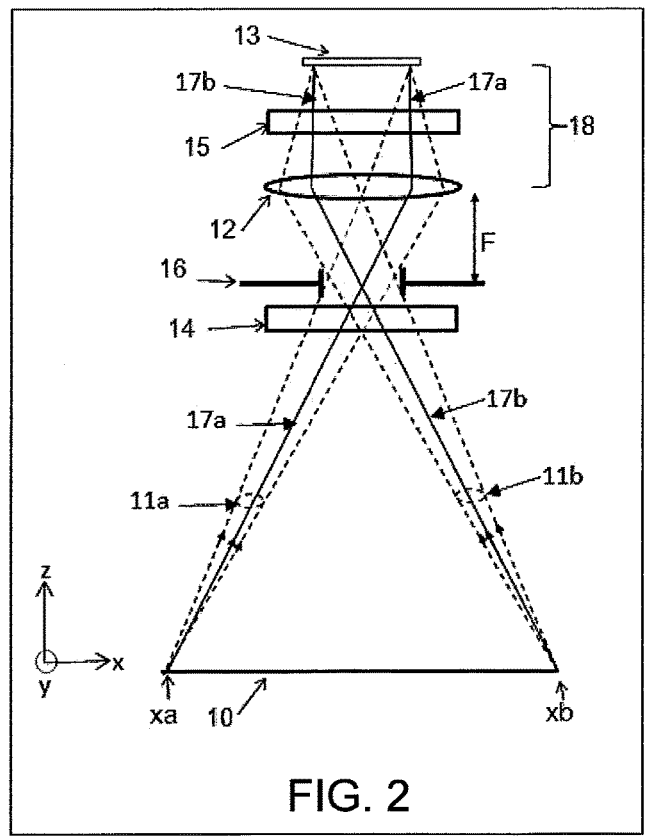
FIG. 2
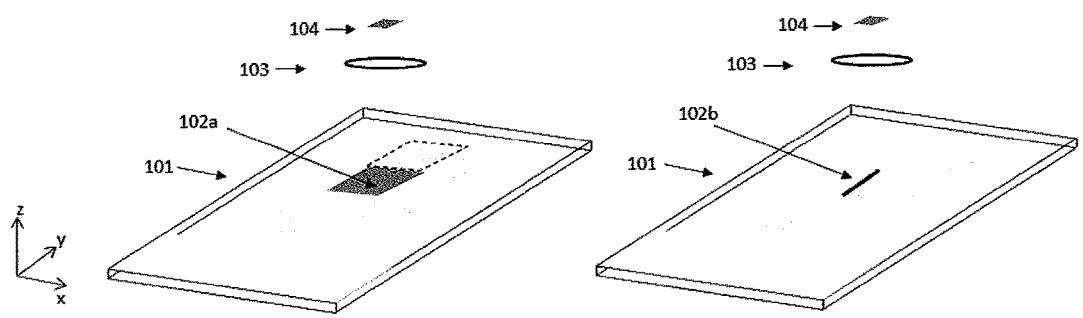
FIG. 3A
FIG. 3B

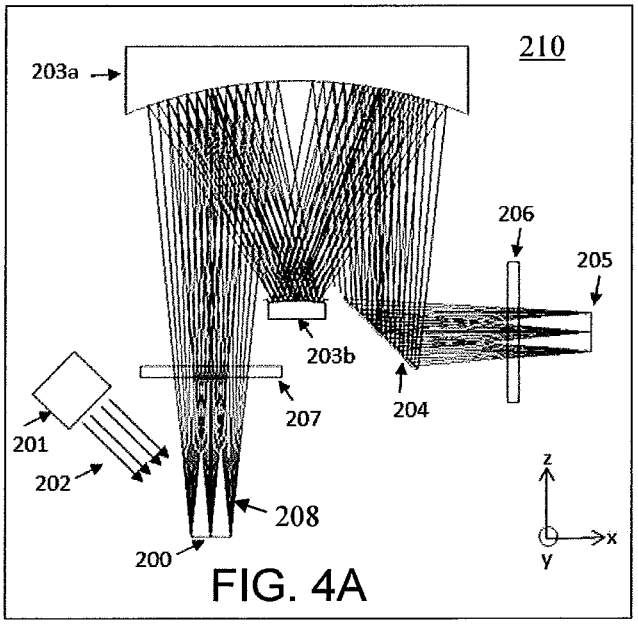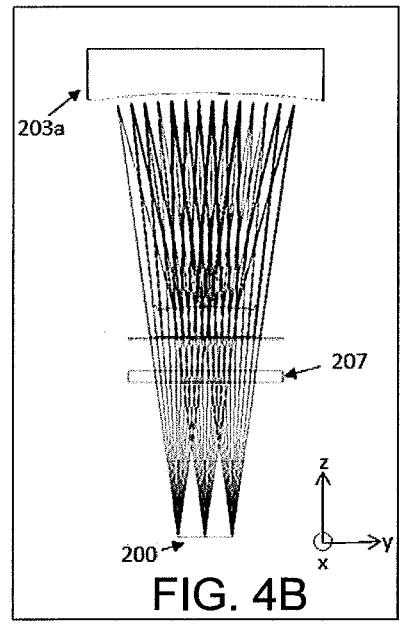
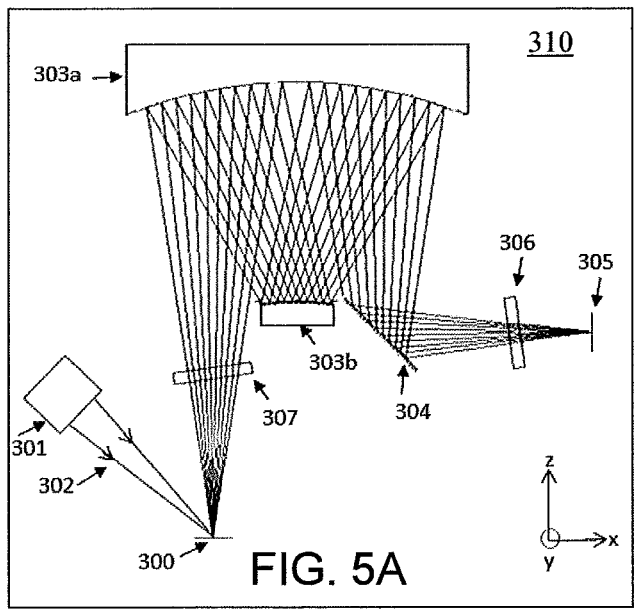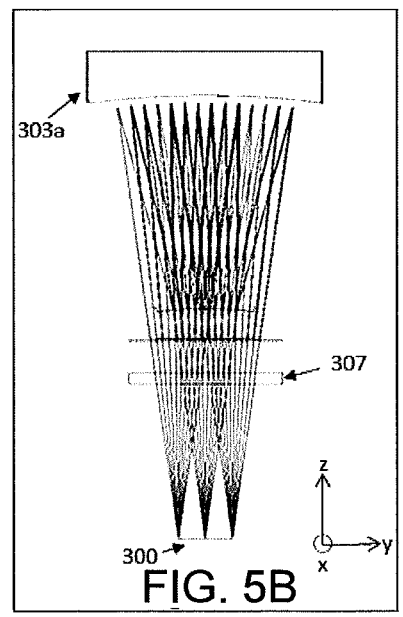

TELECENTRIC, WIDE-FIELD FLUORESCENCE SCANNING SYSTEMS AND METHODS

BACKGROUND

The present disclosure relates to quantitative fluorescence imaging and more specifically to wide-field fluorescence imaging systems and methods. The various embodiments enable accurate, quantitative, fast, contiguous wide-field fluorescence imaging such as laser line scanning with near perfect registration and measurement across the entire field of view.

Recently, there is a growing desire by the scientific research community to include fluorescence detection in tissue imaging tools. Fluorescence detection provides a more controllable, stable way of identifying the impact of certain drugs, for example. A number of automated microscope systems now include fluorescence imaging capabilities. Most of these systems were built by automating the stage of a microscope or adding a microscopic imager to an automated scanner. Their focus has mostly been to automate the tasks that a typical Pathologist performs as he/she inspects a tissue slide under a microscope. This meant that such a system must be a microscope first. Microscopic imaging does provide great benefits, including sub-cellular details and a potential for matching what a Pathologist sees directly through a microscope, but at the same time it tends to be quite slow. A microscope objective images a very small area. For example, a 20× NA=0.75 objective images an area less than 0.5 mm wide at a resolution ~0.4 µm. So, a slide area of 50 mm×25 mm would require 5000 images with stop-and-go tiled imaging. This is generally not a problem for color imaging, like imaging H&E (Hematoxylin and Eosin) stains, since short exposure times are enough to detect the signal. However, for fluorescence imaging, much longer exposure times would be needed for low abundance labeling and therefore these methods result in much longer scan times. Combining the longer scan times with the fact that a typical experiment requires the scanning of a number of slides in order to determine the area of interest to investigate further means that the total processing cycle per experiment can turn into hours if not days.

Of the faster microscope automation techniques is the technique disclosed in U.S. Pat. No. 8,385,619 developed by Soenksen at Aperio Technologies, Inc., now part of Leica Biosystems. Soenksen recognized the need to speed up the automation of slide imaging in microscope systems and implemented line imaging as a way to reduce the number of images to tile (strips). Soenksen used a line scan Time-Delay-Integration (TDI) camera, along with the objective and focusing optics, to image one line at a time. The TDI camera allows for broad illumination (with a lamp or LED) and reads the image as one line at a time. This technique does improve microscope automation and achieves faster scanning results and less tiling mismatch issues. The achieved scan times seem to be acceptable for direct color imaging (H&E stains) where exposure times per imaged line can be short so that the total time it takes to cover a wider area can be reasonable. But, for fluorescence, this technique still requires longer exposure times per line and the result is much longer total scan times. This presents a bottleneck for the cases where there exists a set of slides to go through before the researcher would know if he/she has what he's looking for or not. Based on the time scanning slides takes alone, there is still a need for a fast triage step to determine which slides have the area(s) that would be worth scanning on an automated microscope system. It is desirable for this triage step to be sensitive so it does not miss what can be detected by systems downstream. Also, equally desirable, is the accuracy of the relative location and relative signal reproduction so that accurate assessment of whether or not to go to next steps in the process and if so where exactly to scan at high resolution.

Microscope based systems such as that disclosed in U.S. Pat. No. 8,385,619 allow for "macroscopic imaging" through the use of a lower magnification objective to image a wider field of view per pass and thus cover a larger area in less time. However, this approach suffers from at least two major limitations. First, it requires much longer exposure time per line image because the NA of low magnification objective is much lower than a high magnification objective. For example, a typical 2× objective has an NA less than 0.075 compared to NA=0.75 for 20× which translates to light collection efficiency ~$(0.75/0.075)^2=100$ times smaller. Second, the larger the field of view of a microscope, the more fall-off and distortion there is towards the perimeter of the field of view. This in turn translates into variations in sensitivity across the field of view and inaccurate registration between passes, respectively. These limitations are inherent to the way an objective based imaging system works.

Another key drawback in the existing art for fluorescence imaging, both microscopic and macroscopic, is the variation in signal throughput and optical background suppression across the field of view due to angular spectral shifting of interference filters. The emission spectrum of many fluorescence dyes are narrow and have steep slopes. FIG. 1 shows a typical absorption and emission spectra for LI-COR's IRDye® 800cw. In FIG. 1, a typical long-pass filter that can be used to select a certain window in the emission path is also superposed on the plot. It shows the transmission spectrum of the filter under two incident light conditions: Zero degree angle of incidence (curve 3a) and 20 degree angle of incidence (curve 3b). In most cases for the IRDye® 800cw, the edge for the long-pass filter would need to be placed on the steep slope of the emission curve 2 in order to allow room for excitation light to be matched with the absorption curve 1. This means that if the incidence angle changes when light goes through the filter, the amount of light collected (at that angle) changes. If light collected from different points in the field of view end up going through the filter at different angles, the resultant measurement is not the same even if both locations were illuminated by the same amount of excitation light. Table 1 shows an example of the amount of spectral shifting for a typical interference filter. In many applications this amount is not significant, especially in microscopy applications where there are other more significant factors that may limit its usefulness for quantitative measurements, for example its sensitivity to focus variability. For most microscope systems, including the system disclosed in U.S. Pat. No. 8,385,619, there is no provision to avoid this problem and therefore filters are commonly placed between the objective and the focusing optics where, by definition of imaging by an objective, light from different field points must go through different angles at the side of the objective opposite to the sample side (See, e.g., FIG. 2 of U.S. Pat. No. 8,385,619, element 50 and FIG. 2 of US Patent Application 2011/0121199 to Tanikawa, element 13).

The current inventor realized the need for enhancing background suppression across the whole field of view equally and applied it to imaging small animals. See, e.g., U.S. Pat. No. 7,286,232. FIG. 2 shows one embodiment of this method wherein a telecentric space 18 is created between the imaging optics 12 and the detector array 13 so that light collected from different points on the target 10 go through the emission filter 15 with the same angular range. A rejection filter 14 was also added between the target area 10 and the imaging optics 12 to further enhance the filtering rejection. The telecentric space is created by placing an aperture 16 at the front focal plane of the imaging optics 12. That worked well for that purpose and any similar single shot macro-imaging. There was no need to worry about scanning the target to cover a larger area as is the case here and therefore there was no concern about the angular variation as light goes through the rejection filter as well. The goal then for the rejection filter was to suppress reflected light as an enhancement to the main emission filter which is placed in the telecentric space. There is no clear way to apply this front aperture technique to the rejection filter without sacrificing signal (i.e. reducing the imaging NA) and that's not desirable for low abundance labels such as in tissue sections and tissue arrays.

Others have recognized the usefulness of telecentric projections to achieve various tasks but not with the functions needed here, namely contiguous, wide-field imaging with spectral filtering uniform across the whole field of view. US patent Application 2012/0313008 to Sung-Ho Jo provides a fluorescence detector design that has a telecentric lens positioned between the fluorescence selecting unit (filter) and the light receiving unit (detector). The purpose of using this telecentric lens is to keep lights collected from different wells separate. Hence, this is not an imaging application where a contiguous area or line is imaged at the same time. Besides, the fluorescence selecting unit is still in non-telectric space. A similar design in U.S. Pat. No. 7,687,260 to Gutekunst is provided for collecting light from an array of sites (wells). Here, the telecentric space is created on the object side by using a field lens on top of the wells. This too does not address the filtering variability. Imaging filter 9 (Guntekunst FIG. 1) is still in non-telecentric space. Furthermore, this is not wide-field, contiguous imaging where stricter requirements on distortion and relative positional accuracy are of concern. This technique is neither applicable to the present wide-field imaging problem by itself nor in combination with other above techniques.

Other telecentric based ideas also exist in flow cytometry where, again, it's not a wide-field imaging application. For example, U.S. Pat. No. 8,467,055 to Imanishi discloses use of a lens 48 to create a telecentric space on the detector array side so that the different beams created by a grating 47 enter the detector sites at similar angles. And again, here, there is no concern and therefore no special provisions for where spectral filters are placed.

Therefore, there is still a need for a more robust, quantitative, fast macroscopic fluorescence imager that does not have the limitations of angular dependence on where in the field the light originates from. Furthermore, there is still a need to accurately maintain the relative locations of the origins of fluorescence light on the sample so that multi-pass images are aligned accurately and thus eliminate the focus dependent positional shifting present in current macroscopic wide-field imagers.

SUMMARY

The present disclosure relates to quantitative fluorescence imaging and more specifically to wide-field fluorescence imaging systems and methods.

According to an embodiment, a fluorescence imaging system is provided that typically includes a source subsystem having a sample platform holding a fluorescent material, a light source that illuminates the fluorescent material with excitation light in an absorption band of the fluorescent material, and a first filter that passes wavelengths of light other than the excitation light, the first filter being positioned in a first light path between the sample platform and an entry aperture stop of a bi-telecentric optical imaging system. The fluorescence imaging system also typically includes a detector subsystem for detecting light from the fluorescent material, comprising a light detector having an array of sensing locations, and a second filter that passes wavelengths of light in an emission band of the fluorescent material, the second filter being positioned in a second light path between the light detector and an exit aperture stop of the bi-telecentric optical imaging system. The fluorescence imaging system further typically includes a bi-telecentric optical imaging system comprising imaging optics arranged and positioned such that a first telecentric space is created or exists in the first light path between the sample platform and the entry aperture stop wherein Principal or chief rays from a plurality of field points on the sample platform are parallel to each other when passing through the first filter; and such that a second telecentric space is created or exists in the second light path between the light detector and the exit aperture stop wherein the Principal or chief rays from the plurality of field points are parallel to each other when passing through the second filter. In this manner, light collected from different points in the field of view pass through the first filter at the same angles and also through the second filter at the same angles to thereby reduce or eliminate angular spectral shifting effects.

In certain aspects, the bi-telecentric optical imaging system includes an Offner relay mirror system arrangement comprising a first mirror element having a spherical mirror surface and a second mirror element having a spherical mirror surface, wherein the entry aperture stop and the exit aperture stop each comprise a portion of the first mirror element. In certain aspects, the first mirror element presents a convex-shaped mirror surface, and wherein the second mirror element presents a concave-shaped mirror surface.

In certain aspects, the bi-telecentric optical imaging system comprises a bi-telecentric lens arrangement, wherein the entry aperture stop includes a first refractive lens element and wherein the exit aperture stop includes a second refractive lens element.

In certain aspects, contiguous field points on the sample platform are simultaneously imaged onto contiguous sensing locations on the light detector. In certain aspects, the light detector includes a CCD array detector or other light detector or sensor.

According to another embodiment, a method is provided for imaging a fluorescent material that absorbs light in an absorption band of wavelengths and that emits fluorescent light in an emission band of wavelengths. The method typically includes illuminating a first portion of a fluorescent material on a sample platform with an illumination beam having excitation light in the absorption band, and detecting emissions from the first portion of fluorescent material using a detector system including a light detector having an array of sensing locations, a bi-telecentric optical imaging system, a first filter that passes wavelengths of light other than the excitation light, the first filter being positioned in a first light path between the sample platform and an entry aperture stop of the bi-telecentric optical imaging system, and a second filter that passes wavelengths of light in the emission band, the second filter being positioned in a second light path between the light detector and an exit aperture stop of the bi-telecentric optical imaging system. The bi-telecentric optical imaging system used in the method typically includes imaging optics arranged and positioned such that a first telecentric space exists in the first light path between the sample platform and the entry aperture stop wherein Principal rays from a plurality of field points on the sample platform are parallel to each other when passing through the first filter; and such that a second telecentric space exists in the second light path between the light detector and the exit aperture stop wherein the Principal rays from the plurality of field points are parallel to each other when passing through the second filter, and wherein contiguous field points on the sample platform are simultaneously imaged onto contiguous sensing locations on the detector to form a first detector image.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 2 shows a telecentric space created between the imaging optics and the detector array so that light collected from different points on the target goes through the emission filter with the same angular range.

FIG. 3a depicts area imaging, which includes imaging a whole area at a time.

FIG. 3b depicts line imaging, where one line is imaged at a time.

FIGS. 4a and 4b show a front view and side view, respectively, of a fluorescence imaging system according to one embodiment.

FIGS. 5a and 5b show the front view and side view, respectively, of a fluorescence imaging system according to another embodiment.

DETAILED DESCRIPTION

Figure 1:
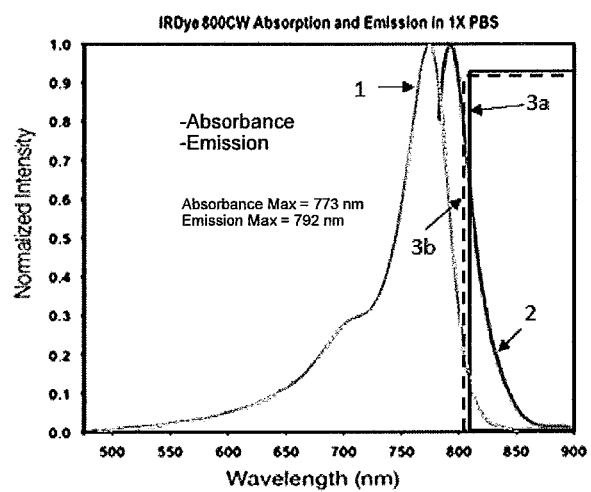
FIG. 1 shows a typical absorption and emission spectra for LI-COR's IRDye® 800cw.

To image in fluorescence, a target (e.g., containing fluorescent material) is illuminated by an optical signal having a first spectral content (excitation light) where a portion of such a signal is absorbed by at least part of the target and re-emitted as optical signal of a second spectral content (emission light). The emission light is then detected by a detection system as a measure of the amount present of that target at that location. Imaging a fluorescently labeled area, therefore, requires excitation light delivered to the target area, an imaging system that collects light from the target area and projects it onto an optical detector (e.g., detector array), and a means to separate the emitted fluorescence light from the portion of excitation light that makes its way through the imaging system. The latter, typically, includes one or more interference filters.

Wide-Field imaging, as considered herein, includes collecting light from a contiguous area and projecting it onto a detector array, such as a CCD or other detector having an array of sensing locations or pixels, at the same time in a way that preserves the relative locations of each point within the contiguous area. This is different from collecting light from one point at a time and sequentially scanning to a different point in order to cover a larger area, i.e. point scan imaging. It is also different from collecting light from a large area and condensing the total amount of light onto a detector and reading it as total signal. The latter is common for many measurement techniques that do not require specific location information.

One skilled in the art will understand that other types of useful sensors or detectors and arrays of sensors, such as CCD and CMOS sensors can be used. Other useful sensors might include photodiodes, avalanche photodiodes, silicon photomultiplier devices, an array of photomultiplier tubes, a focal plane array, etc.

Two types of wide-field imaging include area imaging and line scanning FIG. 3a depicts area imaging, which includes imaging a whole area 102a at a time, the size of which depends on various design factors that include the desired resolution, available components (detectors, imaging lenses, etc. . . . ), cost, sensitivity, and speed. Target areas that are larger than can be imaged in one shot are covered by successively imaging different sub-areas and stitching them together through software. Various technologies exist in this class each optimized for a particular application and/or focusing on a particular benefit. In this depiction, fluorescently labeled target area is on top of sample platform or medium 101 (e.g., a slide) and can cover the whole x-y surface area on the platform or a portion of it. The wide-field imaging system 103 images the sub-area 102a onto the array detector 104. If imaging an area larger than 102a is needed then platform 101 and/or the imaging system are translated along the x- and/or y-direction and additional sub-area images are taken.

FIG. 3b depicts line-scanning, where one line is imaged at a time. The length of line 102b is also dictated by similar design factors as is the case for area imaging. Here, a wide-field imaging system 103 images line 102b in a contiguous manner such that every point along that line is imaged at the same time. The array detector 104 can include one or multiple linear arrays, depending on the specific measurements desired. To cover an area here, typically sample platform 101 and/or the imaging system are translated along the x-axis and then stepped along the y-axis to take another pass.

In both area imaging and line imaging applications, scanning can be achieved by moving the illumination light across the target area while the detection system and the target remain fixed, for example, using a scanning mirror or similar element that sequentially aims the illumination beam at different target locations over time and the detection system is accordingly aimed at these locations. As another example, scanning can be achieved by moving the sample platform relative to a fixed illumination beam and a fixed detection system, or by moving both the illumination and detection systems while holding the sample platform fixed.

Telecentric imaging refers to the case where the chief rays from all the points being images are parallel to each other. A design can be telecentric in the object space where the Principal or chief rays are parallel to each other in the space between the $1^{st}$ element of the imaging optics and the sample. On the other hand, a design that's telecentric in the image space has its Principal or chief rays between the last element of the imaging optics and the detector array parallel to each other. Referring to FIG. 2 again, each point xa, xb along the length of sample 10 generates a cone of light 11a, 11b surrounding a center ray 17a, 17b, called chief ray. This cone of light passes through aperture 16, where chief ray 17a, 17b passes through its center, and is then focused by the imaging lens 12. Because all the chief rays coming from sample 10 pass through the center of aperture 16, which in turn is located at the front focal length of lens 12, these chief rays would be collimated on the other side (detector side) of the lens 12 (creating telecentric space 18). In this manner, all the cones of light will have the same parallel direction, i.e. their chief rays are parallel to each other in telecentric space 18. Accordingly, each of cones of light 11a, 11b and from every point in between will undergo the same filtering effect by filter 15 so that for equal amount of light incident on filter 15 there is equal amount of light exiting it. Another benefit of telecentricity is that when the distance in a telecentric space changes, for example between lens 12 and detector 13 in FIG. 2, then the distance between the chief rays at the detector 13 remains unchanged. This is not the case for non-telecentric side between aperture 16 and sample 10. If the front distance between aperture 16 and sample 10 changes, both the focus changes but also the distances between where chief rays 17a, 17b, and every one in between hit sample 10 change as well which makes scaling on that side sensitive to focus errors.

FIGS. 4a and 4b show a front view and side view, respectively, of a fluorescence imaging system 210 according to one embodiment. Fluorescence imaging system 210 as depicted includes an Offner relay mirror system having a primary mirror element 203a and a secondary mirror element 203b that together create a bi-telecentric 1:1 imaging system that approaches perfect imaging. Mirror elements 203a and 203b each present a generally spherical mirror surface, at least where light interacts with each element. This design leverages the symmetry present in this mirror system to create both object-space and image-space telecentric areas, enabling placement of both a rejection filter 207 and an emission filter 206 as depicted without sacrificing any light collection capability or imaging performance. For example, as shown, rejection filter 207 is positioned in the object-space telecentric area and the emission filter 206 is placed in the image-space telecentric area. In this manner all filtering is done with chief rays parallel to each other and distances between chief rays is unchanged when adjusting focus. The magnification of this imaging technique, and therefore location accuracy, is quite insensitive to focus errors and therefore image-to-image or pass-to-pass registration is very robust. The aperture stop defines the size of the cone of light collected by or admitted to the optical system. As shown in FIG. 4a, mirror element 203b acts as both the entry aperture stop and the exit aperture stop. That is, the object-space telecentric area is created or exists in the light path between the sample platform 200 and the portion of mirror element 203b defining the entry aperture stop, and the image-space telecentric area is created or exists in the light path between the detector 205 and the portion of mirror element 203b defining the exit aperture stop. The aperture stop is also where the chief rays pass through its center, i.e., cross the optical axis (for mirrors, light changes direction after it hits a mirror); mirror element 203b is where chief rays hit in the center (optical axis of that mirror).

In certain aspects, rejection filter 207 includes one or more filter elements that reject (or filter out) excitation light wavelengths, while allowing other light wavelengths as desired to pass. Similarly, emission filter 206 includes one or more filter elements that allow emission band wavelengths to pass, while rejecting other wavelengths as desired. Examples of useful filters include notch filters to block most of the excitation light and band-pass filters to further block any residual excitation light leaking through the notch filter.

Referring to FIG. 4a, a light source 201 generates an excitation light beam 202, preferably nearly collimated, that illuminates a portion of the sample area 200. Light source 201 may include a laser source (e.g., diode laser or other laser source), an LED, a broadband lamp, etc, and appropriate optional optical elements to shape the light beam as desired. The excitation light beam 202 may be configured to illuminate an area on the sample for area imaging applications as depicted, or it may be configured to illuminate a line on the sample for line scanning applications. From every point on the sample area 200 being imaged, there is a cone of light 208 that includes a chief ray at its center that passes through rejection filter 207 in a telecentric way, the chief ray is refocused by Offner mirror elements 203a and 203b to the image side where the chief ray passes through emission filter 206 also in a telecentric way before it reaches detector array 205, also perpendicularly to it, in a telecentric way. Optional folding mirror 204 is used to redirect the path for ease of packaging. FIG. 4b shows that imaging is telecentric in the y-z plane as well. With this imaging system, a strip area can be imaged in fluorescence under fully telecentric filtering conditions. Larger sample areas are covered by scanning the sample platform or the imaging system to other different areas and stitching all images together to produce a uniform, contiguous image of the desired total area.

FIGS. 5a and 5b show the front view and side view, respectively, of a fluorescence imaging system 310 according to another embodiment. Fluorescence imaging system 310 includes a laser line scanning version of the all-telecentric Offner-based fluorescence relay system. Referring to FIG. 5a, a light source 301, such as a laser line source, generates excitation light and emits a focused line-shaped beam and projects it onto sample 300. The laser line is preferably shaped to focus on a line perpendicular to the plane of incidence, wherein the illuminating line is substantially uniform along its length and narrow in the other direction, for example diffraction limited. The fluorescence signal generated by this excitation line produces a cone of light from every point along that line with a chief ray at its center which passes through filter 307 in a telecentric way, re-imaged to the other side by the Offner relay mirrors 303a and 303b, passes through the emission filter 306, also in a telecentric way, and impinges upon the detector array 305 also in a telecentric way. FIG. 5b shows a y-z plane view which shows that the telecentric space in this embodiment is along the line being imaged which is along the y-axis. The width of the line in the x-direction is small, defined by the required scan step resolution. For example, for 5 μm scan resolution, the width of the line is about 5 to about 20 μm wide. The length of the line is matched to the length of the detector array or slightly longer (e.g., typically on the order of about 1 mm to about 10 mm).

The laser line scanning embodiment presents a number of additional advantages. For example, in US 2012/0257087, which is hereby incorporated by reference in its entirety, a laser differential scan method is provided that reduces optical background from scattering type media such as tissue or membrane as well as the optical components in the imaging path. This type of improvement can also be integrated in the present embodiments to further enhance the sensitivity of the system. This is done through the use of a detector array where two line images are simultaneously acquired for every laser illumination position, one at the laser illumination location and another in neighboring regions where the main excitation beam does not reach. The latter is read as a line image of the background and is subtracted from the fluorescence line image. The resulting difference contains fluorescence signal and minimal background signal.

Additional benefits of laser line scanning includes the availability of one direction (e.g., x-z plane) to tilt signals reflected by the filters away from the imaging path to further reduce background without negatively affecting the imaging performance along the line (e.g., y-z plane). In FIG. 5a, rejection filter 307 is shown as being tilted (e.g., tilt angle can be about 4 to about 8 degrees or more) so that most of its reflection falls away from the measurement area at sample 300. Also, emission filter 306 is similarly tilted in the x-z plane so that its reflection does not go back through the Offner imaging relay and reach sample 300.

Yet another benefit of the Offner relay system is its reflective nature and therefore it is achromatic which makes it ready for combining more than one color without the need for any color related adjustments or corrections.

An example of the components that can be used in the embodiment represented by FIGS. 5a and 5b include:

303a Front surface concave mirror with radius of curvature R=80 mm
303b Front surface convex mirror with radius of curvature R=40 mm
304 Front surface flat mirror
305 CCD detector
306 Emission Band-Pass filter, example 510 nm to 550 nm.
307 Rejection filter, example 500 nm Long-Pass.

Figure 6A:
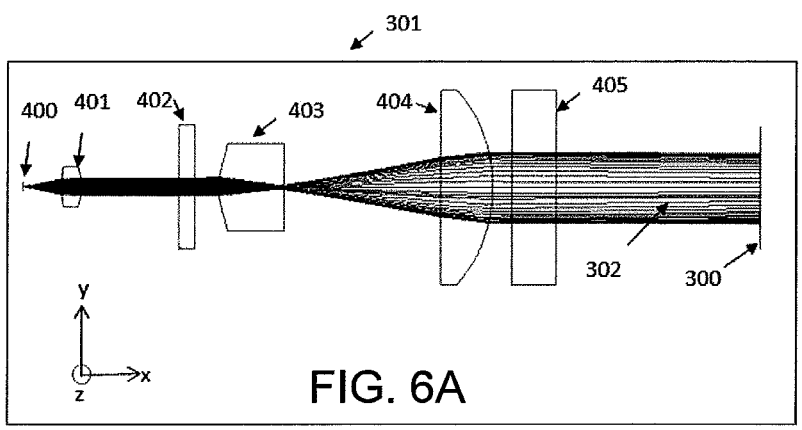
FIGS. 6a and 6b show an example of a laser line generator 301 that can be used with the embodiment shown in 5a and 5b
Figure 6B:
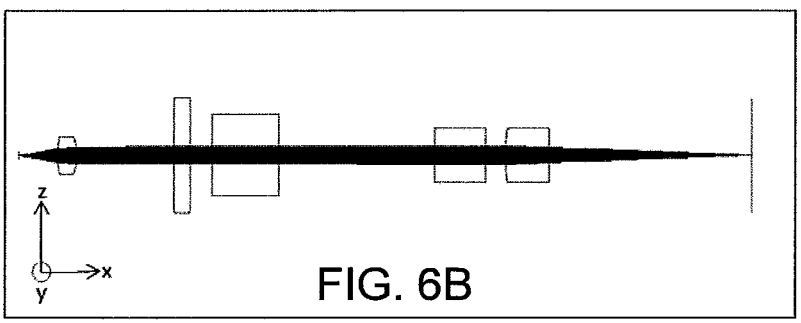
Figure 7:
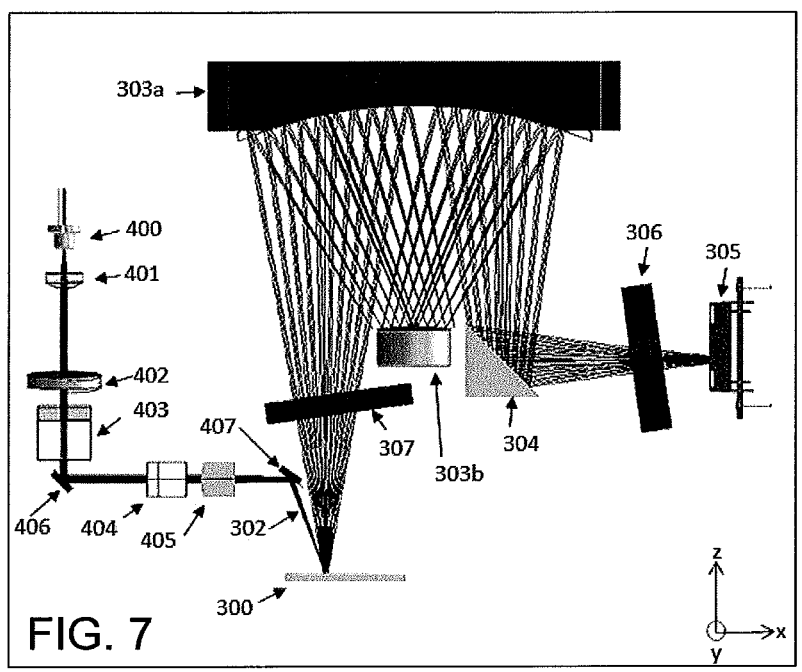
FIG. 7 shows the line generator optical elements of FIGS. 6a and 6b combined with the bi-telecentric, line imaging optical elements of FIGS. 5a and 5b together in one system according to an embodiment.

FIGS. 6a and 6b show an example of a laser line generator 301 that can be used with the embodiment shown in 5a and 5b. Laser line generator 301 includes a laser diode based system that generates a uniform laser line 302 and focuses it onto the sample plane 300. A laser diode 400 is collimated by a collimating lens 401, and passes through an excitation filter 402. The collimated, filtered output from filter 402, which typically is in the form of a Gaussian beam, enters next into a Line Generator lens 403 and then cylindrical lens 404 and cylindrical lens 405 to produce a collimated, uniform line which has a nearly flat-top (uniform) profile along the line length and Gaussian in the other direction. This collimated line is then focused in the Gaussian-beam plane onto the sample plane 300. Example of the components that can be used in the embodiment represented by FIGS. 6a and 6b are:

400 Laser diode, example Nichia's 488 nm laser diode.
401 Aspheric lens
402 Band-Pass filter centered at laser diode wavelength
403 Powell lens
404 Cylindrical lens, example F=12.5 mm
405 Cylindrical lens, example F=15 mm FIG. 7 shows the line generator optical elements of FIGS. 6a and 6b combined with the bi-telecentric, line imaging optical elements of FIGS. 5a and 5b together in one system. Additional mirror elements 406 and 407 are included to redirect beam 302 as depicted.

Figure 8B:
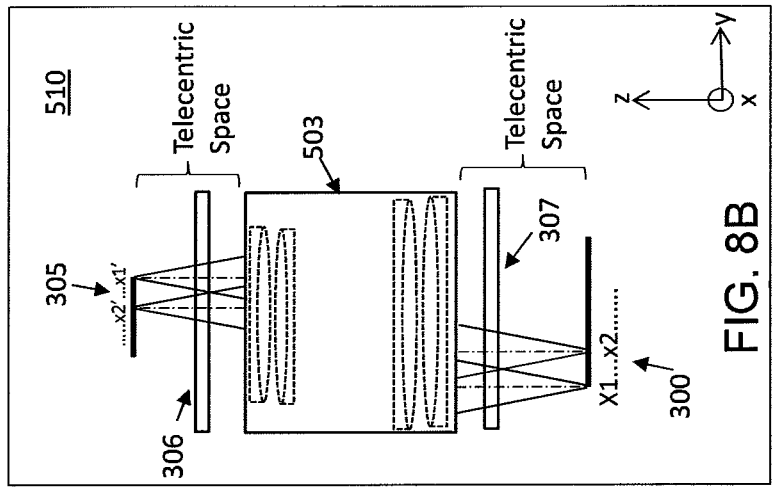
FIGS. 8a and 8b show a front view and side view, respectively, of a fluorescence imaging system according to another embodiment.
Figure 8A:
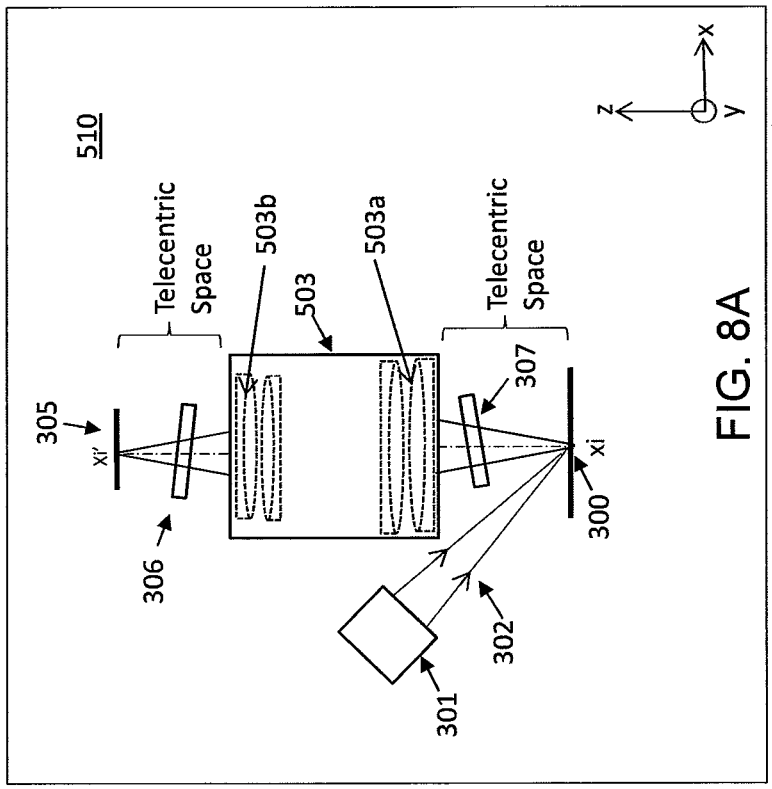

FIGS. 8a and 8b show a front view and side view, respectively, of a fluorescence imaging system 510 according to an embodiment. Fluorescence imaging system 510 as depicted includes a bi-telecentric lens-based optical imaging system 503 having a first refractive lens element 503a and a second refractive lens element 503b. Lens element 503a includes an entry aperture stop wherein a telecentric space is created between target platform 300 and lens element 503a. Similarly, lens element 503b includes an exit aperture stop wherein a telecentric space is created between lens element 503b and detector 305. Both aperture stops can be the same or similar. A rejection filter 307 is positioned in the object-space telecentric area and the emission filter 306 is placed in the image-space telecentric area. In this manner all filtering is done with chief rays parallel to each other and distances between chief rays is unchanged when adjusting focus. Similar to FIG. 5a, light source 301, such as a laser line source, generates excitation light and emits a focused line-shaped beam and projects it onto sample 300.

It should be understood that the first refractive lens element and the second refractive lens element can each include more than one lens element. It should also be understood that the first aperture stop and the second aperture stop can each be in air, or located before all the lenses within the first and second refractive lens elements, respectively, or somewhere in the middle of the first and second refractive lens elements, respectively, or after all the lenses within the first and second refractive lens elements, respectively. For example, a lens element within a refractive lens element may include an aperture stop.

Figure 9B:
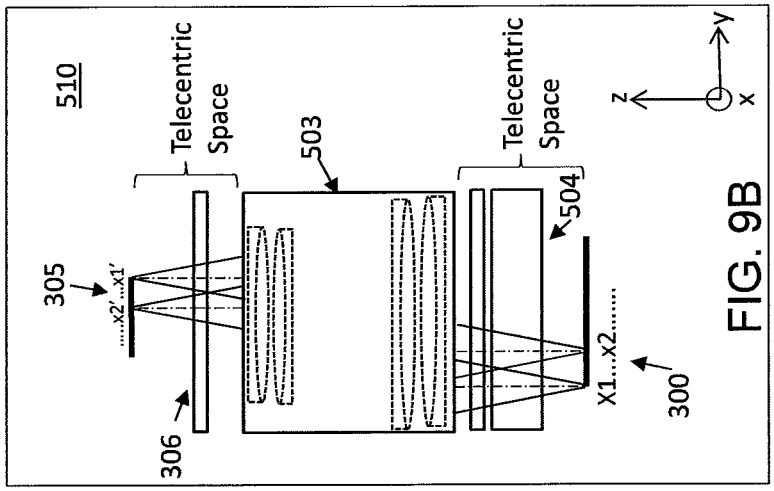
FIGS. 9a and 9b show a front view and side view, respectively, of a fluorescence imaging system according to another embodiment.
Figure 9A:
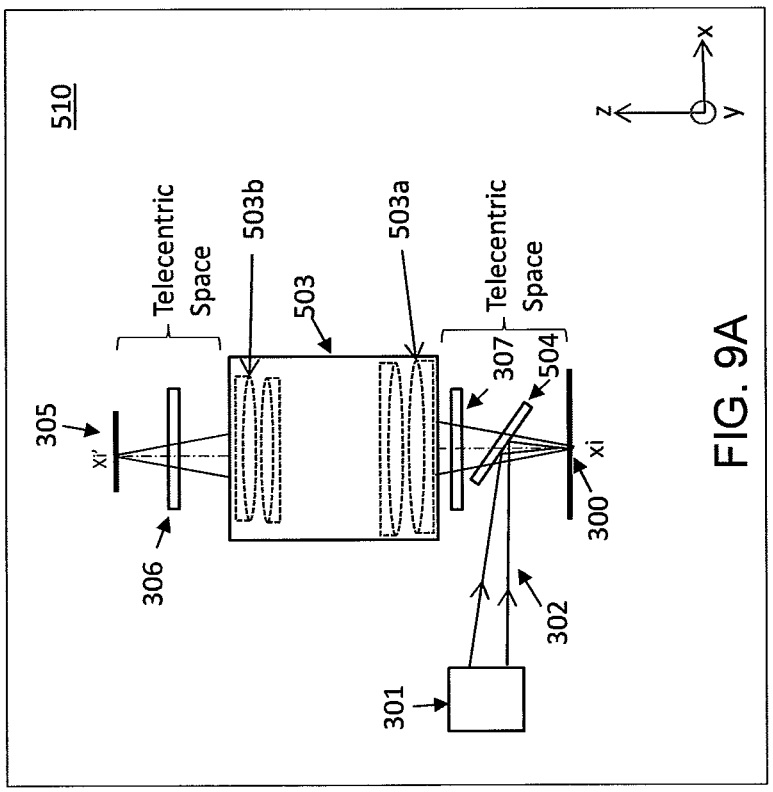

FIGS. 9a and 9b show a front view and side view, respectively, of a fluorescence imaging system 510 according to an embodiment. The configuration shown in FIG. 9 is similar to that shown in FIG. 8, with the addition of a dichroic filter element 504 positioned to reflect excitation light beam 302 towards the sample 300. Fluorescence light emitted at sample 300 passes through dichroic filter element 504 to reach bi-telecentric imaging system 503. Dichroic filter element 504 is also in a telecentric space and therefore its spectral filtering affects all points within a contiguous area or line the same way. It should be appreciated that the configurations shown in FIGS. 8 and 9 are applicable for area imaging and line imaging applications.

All patents, patent applications and other references mentioned herein are herby incorporated by reference in their entireties.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:
1. A fluorescence imaging system, comprising:
  a source subsystem having:
    a sample platform holding a fluorescent material;

a light source that illuminates the fluorescent material with excitation light in an absorption band of the fluorescent material; and a first filter that passes wavelengths of light other than the excitation light, the first filter being positioned in a first light path between the sample platform and an entry aperture stop of a bi-telecentric optical imaging system;

a detector subsystem for detecting light from the fluorescent material, comprising;

a light detector having an array of sensing locations; and a second filter that passes wavelengths of light in an emission band of the fluorescent material, the second filter being positioned in a second light path between the light detector and an exit aperture stop of the bi-telecentric optical imaging system; and the bi-telecentric optical imaging system comprising imaging optics arranged and positioned such that a first telecentric space exists in the first light path between the sample platform and the entry aperture stop wherein Principal rays from a plurality of field points on the sample platform are parallel to each other when passing through the first filter; and such that a second telecentric space exists in the second light path between the light detector and the exit aperture stop wherein the Principal rays from the plurality of field points are parallel to each other when passing through the second filter, wherein contiguous field points on the sample platform are simultaneously imaged onto contiguous sensing locations on the light detector.

2. The imaging system of claim 1, wherein the bi-telecentric optical imaging system comprises an Offner relay mirror system arrangement comprising a first mirror element having a spherical mirror surface and a second mirror element having a spherical mirror surface, wherein the entry aperture stop and the exit aperture stop each comprise a portion of the first mirror element.

3. The imaging system of claim 2, wherein the first mirror element presents a convex-shaped mirror surface, and wherein the second mirror element presents a concave-shaped mirror surface.

4. The imaging system of claim 1, wherein the bi-telecentric optical imaging system comprises a bi-telecentric lens arrangement, wherein the entry aperture stop includes a first refractive lens element and wherein the exit aperture stop includes a second refractive lens element.

5. The imaging system of claim 1, wherein the light source emits a beam of uniform illumination having a line-shaped profile when impinging on the fluorescent material.

6. The imaging system of claim 1, wherein the light source comprises a diode laser.

7. The imaging system of claim 1, wherein the light detector comprises a CCD array detector.

8. The imaging system of claim 7, wherein the contiguous field points on the sample platform are simultaneously imaged onto contiguous sensing locations on the CCD array detector.

9. A method of imaging a fluorescent material that absorbs light in an absorption band of wavelengths and that emits fluorescent light in an emission band of wavelengths, the method comprising:

a) illuminating a first portion of a fluorescent material on a sample platform with an illumination beam having excitation light in the absorption band; and b) detecting emissions from the first portion of fluorescent material using a detector system including a light detector having an array of sensing locations, a bi-telecentric optical imaging system, a first filter that passes wavelengths of light other than the excitation light, the first filter being positioned in a first light path between the sample platform and an entry aperture stop of the bi-telecentric optical imaging system, and a second filter that passes wavelengths of light in the emission band, the second filter being positioned in a second light path between the light detector and an exit aperture stop of the bi-telecentric optical imaging system, wherein the bi-telecentric optical imaging system includes imaging optics arranged and positioned such that a first telecentric space exists in the first light path between the sample platform and the entry aperture stop wherein Principal rays from a plurality of field points on the sample platform are parallel to each other when passing through the first filter; and such that a second telecentric space exists in the second light path between the light detector and the exit aperture stop wherein the Principal rays from the plurality of field points are parallel to each other when passing through the second filter, and wherein contiguous field points on the sample platform are simultaneously imaged onto contiguous sensing locations on the detector to form a first detector image.

10. The method of claim 9, further including moving one or both of the sample platform and the illumination beam in a direction substantially parallel with a surface defined by the sample platform so as to illuminate a second portion of the fluorescent material, and repeating the step of detecting to form a second detector image.

11. The method of claim 10, further including combining the first and second detector images.

12. The method of claim 9, further including repeatedly moving one or both of the sample platform and the illumination beam in a direction substantially parallel with a surface defined by the sample platform so as to illuminate a multiple portions of the fluorescent material, and repeating the step of detecting to form multiple second detector images, and combining the first detector images and the multiple second detector images.

13. The method of claim 9, wherein illuminating includes shaping an output of a laser beam so that the beam has a line-shaped profile where it impinges on the sample platform.

14. The method of claim 9, wherein the bi-telecentric optical imaging system comprises an Offner relay mirror system arrangement including a first mirror element having a spherical mirror surface and a second mirror element having a spherical mirror surface, wherein the entry aperture stop and the exit aperture stop each comprise a portion of the first mirror element.

15. The method of claim 9, wherein the bi-telecentric optical imaging system comprises a bi-telecentric lens arrangement, wherein the entry aperture stop includes a first refractive lens element and wherein the exit aperture stop includes a second refractive lens element.

16. The method of claim 9, wherein the light detector comprises a CCD array detector.

* * * * *